United States Patent [19]
Dumbeck

[11] Patent Number: 5,153,520
[45] Date of Patent: Oct. 6, 1992

[54] IDENTIFYING AND QUANTIFYING THE PRESENCE OF ALPHA RADIATION AND SPECIFIC GASEOUS MOLECULES PRESENT IN AIR SAMPLES

[76] Inventor: Robert F. Dumbeck, P.O. Box 548, Elgin, Tex. 78621

[21] Appl. No.: 557,098

[22] Filed: Jul. 25, 1990

Related U.S. Application Data

[63] Continuation-in-part of Ser. No. 9,520, Feb. 2, 1987, Pat. No. 4,972,081, which is a continuation-in-part of Ser. No. 657,185, Oct. 8, 1984, abandoned.

[51] Int. Cl.⁵ ............................................. G01N 27/66
[52] U.S. Cl. ..................................... 324/469; 342/464; 250/384
[58] Field of Search ............... 324/469, 464, 71.1, 324/459, 465, 466, 467, 468; 250/384, 381, 382, 253; 73/23.21, 23.35

[56] References Cited

U.S. PATENT DOCUMENTS

| | | | |
|---|---|---|---|
| 4,041,376 | 8/1977 | Furuto et al. | 324/469 |
| 4,053,825 | 10/1977 | Young | 324/469 |
| 4,705,947 | 11/1987 | Ramsey et al. | 250/384 |

FOREIGN PATENT DOCUMENTS

| | | | |
|---|---|---|---|
| 493670 | 10/1938 | United Kingdom | 324/469 |
| 810062 | 3/1959 | United Kingdom | 324/469 |

*Primary Examiner*—Kenneth A. Wieder
*Attorney, Agent, or Firm*—Laurence R. Brown

[57] ABSTRACT

Means and methods of detecting particular particles in an air stream at very low concentration levels and identifying the particles and magnitude of concentration are afforded. Thus, a particle detector cell has a source of ionizing radiation of constant magnitude, an anode and cathode for moving ions through a radiation activity region and a detector electrode for capturing and measuring free electrons as a dynamic signal indication of the presence of particular particles in the activity region. Particular gas molecules are identified by their fingerprint, namely a spectral response to resonating frequency of electrons orbiting in their molecular structure. The magnitude of free electrons detected determine the concentration of the particles present in air. The output may be recorded on a strip chart for identification and quantification or may be logged in a digital computer. The computer may organize a frequency scanning procedure correlated with dynamic free electron activity for digital storage and recall, and for comparison with spectrum tables for identification of molecules present in an air stream. The detector is very sensitive to low concentration levels of particles such as a few microcuries of alpha particles per liter of air, with equivalent detection of particular gas molecules which can be ionized in the presence of r-f fingerprinting frequencies.

15 Claims, 8 Drawing Sheets

IDENTIFYING AND QUANTIFYING THE PRESENCE OF ALPHA RADIATION AND SPECIFIC GASEOUS MOLECULES PRESENT IN AIR SAMPLES This application is a continuation-in-part of my co-pending application Ser. No. 07/009520 filed Feb. 2, 1987, for Detection of Contaminants in Air, now U.S. Pat. No. 4,972,081 issued Nov. 20, 1990 which in turn was a continuation-in-part of Ser. No. 657,185 filed Oct. 8, 1984, now abandoned.

TECHNICAL FIELD

This invention relates to detection of alpha radiation and other charged particles, and more particularly it relates to sensitive electronic instrumentation for detecting and measuring low levels of charged particle concentration in air flow streams to identify and quantify trace ingredients carried in the air flow streams such as alpha radiation and particular gaseous molecules.

BACKGROUND ART

In my above mentioned patent, trace amounts of radon in air streams are detected and measured by means of sensitive electronic alpha detector instrumentation. This invention is directed to the identification or fingerprinting of various trace ingredients including alpha particles and particular gas molecules carried in air flow streams in small concentrations, by interacting the air flow streams with an alpha radiation activity region of a constant known magnitude.

Various types of electronic detectors for identifying ingredients found in air are known in the prior art, as exemplified by the U.S. Patents now briefly described.

D. M. Mechlenburg in U.S. Pat. No. 4,616,501 issued Oct. 14, 1986 measures gas concentrations in air, such as Freon, by means of ultrasonic mechanical energy of at least two frequencies to be propogated into a chamber containing a known gas in unknown concentration, and measures the profile amplitude of the ultrasound energy at selected points in the chamber. This system however cannot detect and identify an unknown ingredient in air.

R. N. Compton, et al. in U.S. Pat. No. 3,803,481 issued Apr. 9, 1974 and C. F. Robinson in U.S. Pat. No. 2,820,946 issued Jan. 21, 1958 employ negative ion detectors to determine leakage of gases such as Freon. However the ion detector must be operated in a vacuum and thus does not not accomodate measurements directly in the atmosphere. Nor, does it identify unknown ingredients in air.

E. A. Jeffers in U.S. Pat. No. 4,609,875 uses a corona discharge to create an ion stream for determining concentrations of Freon in air. High voltage corona type devices are subject to drastic variation in the presence of varying humidity and operating voltages and are very difficult to make accurate and sensitive to small traces of monitored gases, and cannot distinguish unknown kinds of ingredients of air. Also high voltages necessary for operation do not permit small compact self contained instruments to be produced at reasonable prices.

Peter J. Chantry, et al. in U.S. Pat. No. 4,007,624 issued Feb. 15, 1977 provides a gas detector uses laser energy or heat energy to excite gas molecules to induce vibrations dissociating electrons from orbit. Identification of gases is achieved by tuning the laser frequency to excite particular molecules of interest. Migrating electrons are measured in a vacuum system that is not adapted to measurement of undiluted air flow directly. Thus accurate quantitative measurements are not feasible with such detectors.

Malcolm R. Uffelman in U.S. Pat. No. 4,385,516 detects and identifies chemical vapors in atmospheric air by means of radio frequency radiation tuned to the resonance absorption frequency of particular molecules sent into the atmosphere for reflection and reception in modified form to determine the absorption spectrum which can identify specific molecules present. This technique is advantageous in permitting atmospheric air to be tested, and in identifying unknown molecules present in air. It is however only applicable to mass clouds, and could not be used to determine small traces of molecules present in a small volume of air. Futhermore, it is subject to many kinds of interference with signals and electromagnetic noises in the atmosphere that could lead to erroneous and inaccurate analysis and quantitative measurements.

James E. Lovelock, et al. in U.S. Pat. No. 3,634,754 attempts to make accurate quantitative measurements of carrier gases flowing through an ionizing detector with a tritium ionizing source therein. Electron absorbing molecules are thus quantitatively measured by means of measurements of ion migration through a gas being tested. There is no way to identify a particular gas molecule other than that it is one which captures electrons. Problems occur in the ion field which of itself detracts from accurate measurements by opposing variations caused by concentrations of the gas molecules. This is compensated for by varying the frequency of electron pulses as a function of the sensed signal current and then counting the number of pulses as a quantitative measurement of gas concentration. This equipment cannot accurately detect and qualify small traces of pollutant gases in air for example because of the problems of detection of ions migrating between anode and cathode electrodes by means of anode to cathode currents.

There is not available in the prior art a system which can both identify precisely different unknown molecules present in small concentrations in an air sample and produce an accurate quantitative measurement of the different molecules.

There is not available in the prior art any accurate alpha radiation detector operable in atmospheric air and environment to give direct readings of magnitude of very low concentrations of alpha radiation without errors due to other types of radioactive radiation, contaminants in the air or environmental conditions affecting the detector operation.

It is a general objective of this invention to resolve the foregoing shortcomings of the prior art detectors and to provide instrumentation capable of identifying and/or quantitively measuring the concentration of unknown gas molecules present in air samples.

A more specific object of the invention is to provide improved electronic instrumentation for identifying molecular constituency of undiluted atmospheric air flowing through the instrument and for quantitatively measuring magnitudes of identified selectively ionizable molecules for a wide range of concentrations from very small traces to significant percentages of the sampled air.

DISCLOSURE OF THE INVENTION

An electronic alpha radiation detector cell and operation system is provided with the capability of isolating and measuring alpha radiation directly at very high sensitivity and with very high quantitative accuracy, yet surprisingly simple in structure and low in cost. The detector responds solely to alpha radiation and not to other forms of radioactive radiation, such as gamma rays and the like. It is characterized by an alpha emission standard providing a region constant level of alpha radiation activity in a region between an anode and cathode for migrating ions through the region, and detection of interacting activity in the field by a third free electron capture electrode positioned in the region.

Accuracy in quantitative measurements is achieved in part by means of a calibrated standard alpha emitter source such as a radioisotope, and in part by means of a dual arrangement of cells connected to offset possible inaccuracies due to environmental factors such as temperature or air contaminants and those due to instabilities in dynamic electronic operating parameters of the cell such as voltage variations and disturbances in electric or electromagnetic fields, etc.

The basic electronic detector cell configuration is essentially a triode operable in air atmosphere with a cathode, anode and detector electrode wherein an alpha particle stream of calibrated magnitude establishes a reference current flow berween cathode and anode electroded bridging an alpha particle activity region. The conditions in the alpha particle activity region are monitored by an intercepting detector electrode for measuring free electron activity in the region. Thus, variations caused by means of intrusion of impurities or gaseous molecules in air introduced into the alpha particle activity region in the cell of very low magnitude may be detected and quantified. The increase in alpha particle activity caused by alpha radiation is sensed to quantify external alpha radiation introduced from an external environment into the cell. Other dynamic changes such as by introduction of ionized particles into the region are sensed by the detector electrode as they occur in the region of alpha particle activity with the cell.

The instrument is so sensitive to small concentrations of alpha radiation of the order of less than 4 microcuries per liter of air that a fourth sesitivity control electrode is used for extending the range by inhibiting sensitivity and thereby preventing saturation of the cell from strong radiation fields.

This cell is used in a narrow band detection mode, herein called fingerprinting, for identifying and quantifying unknown gaseous molecules present in air flow samples, by means of introduction of electromagnetic radiation energy of known narrow band vibration frequencies capable of identifying orbital resonances and thus inducing orbital expulsion of electrons to ionize only the fingerprinted gases for affecting the dynamic response of the detector electrode to the introduction of those particular molecules in the presence of identifying frequency fingerprints. For such operation of the detector cells, particular attention is given to the physical dimensions consistent with the very high frequency radio waves of short wavelength processed within the cell in the alpha particle activity region. Thus the cells are very small in dimension.

Output currents for the detector electrode for identification of and quantification of the particular molecules may be recorded on a strip recorder. In this manner an inexpensive portable spectrascope is provided capable of determining particular gaseous contaminants or constituents of an air stream in trace amounts, including Freon, benzine and like gases in the conventional unionized atmospheric form mixed in air, whose presence are not readily detected in very small trace amounts in the prior art without expensive laboratory spectrometers or in devices operable only in a partial vacuum.

In essence the detector responds to dynamic changes of current flow at the detector electrode due to alpha radiation activity in a wide band mode without external electromagnetic radiation influence or significant instrument errors. Thus, the dynamic response of the detector electrode in the alpha activity region of the detector responds in a wide band mode which detects either alpha radiation or selective narrow band harmonically ionized molecules caused in the presence of specific resonance frequencies identifying the particular molecule (its fingerprint frequency) in a narrow band mode employed in the presence of induced electromagnetic radiation influence.

Other features, objects and advantages of the invention will be found throughout the following description, claims and accompanying drawings.

BRIEF DESCRIPTION OF THE DRAWINGS

Like reference characters refer to similar features in the various views of the accompanying drawing, wherein.

THE PREFERRED EMBODIMENTS

Figure 1:
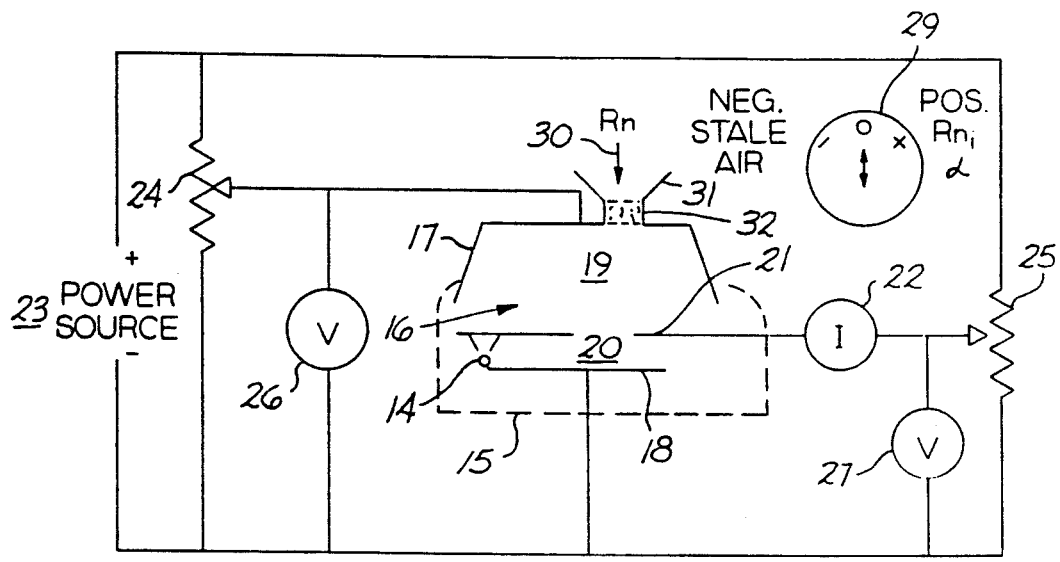
FIG. 1 is a schematic circuit diagram of an alpha detector embodiment of the invention.

In the detector configuration of FIG. 1, the detector contained within a vessel 15 has an ionized region, induced by alpha particle activity of constant magnitude, confined within a chamber 16 defined by a set of electrodes 17, 18. The internal cell alpha particle activity is produced by an internally located calibrated radioisotope source standard 14 which emits alpha particles. An ion stream thus migrates between anode and cathode electrodes 17, 18. The outer anode electrode 17 is exposed for contact with an air environment at atmospheric pressure and defines a first chamber compartment 19. Air at atmospheric pressure, which has unknown constituents and molecules, possibly radon or some other source of alpha particle radiation for providing external alpha particles or trace concnetrations of a pollutant gas, serves as a carrier medium for unkown molecules and the access opening 31 permits entry of an air stream and radiation. Thus, unknown radiation and air constituents can enter chamber 16 wherein with internal alpha particles from source 14 a region of alpha particle activity is monitored by means of detector electrode 21 imposed between the anode electrode 17 and the cathode electrode 18 to capture free electrons as an indication of the ionization in the region and dynamic changes in ionization caused by introduction of specific ions such as alpha particles or pollutant gas molecules.

The cathode electrode 18 and anode electrode 17 define a chamber compartment 19, 20 in which ions migrate at a constant known magnitude established by the emitter source 14. Alpha particle activity in this region is a dynamic resulting from the influence of ions carried by an air flow stream therethrough. This dynamic change is monitored by current 22 (I) response to free electron capture characteristics of the detector electrode 21. Alpha particles emanating from the standard radiation source 14 are present in the static or steady state reference mode to permit the detector electrode 21 to sense very small dynamic current deviations in the alpha particle activity region within the chamber 16, which are caused by the capture of free electrons by detector electrode 21. Thus, by means of current readings at ammeter 22 or other electronic measuring means a quantitative output signal may be produced. The power supply 23 provides operating potentials for the electrodes, which can be varied by means of potentiometers 24 and 25 to a value represented by voltmeters 26, 27.

The vessel 15 contains appropriate means such as opening 31, which may be filtered (32) to remove moisture, dust, etc. Thus, the alpha particle activity region 16 is exposed to the influence of ambient air at atmospheric pressure and external radiation sources capable of influencing the alpha activity region monitored by the detector electrode 21 via the current I (22) flow, which can be quantitatively measured with a high degree of accuracy. Since the standard source 14 of alpha emission is a steady reference value, extremely small changes in the alpha particle activity are measurable with high quantitative accuracy as a function of current flow I (22). External alpha radiation of small magnitudes for example which passes through the entranceway 31 into the alpha activity region 16 are directly measured quantitatively by the current magnitude I (22) characteristics.

Note that the detection instrumentation cell is substantially that commercially available from the Amersham company, 2836 So. Clearbrook Drive, Arlington Heights, Ill., 60005, along with details of their operating characteristics including the specifications of the radioisotope standard 14, all at a low commercial price, since these units have in the prior art been used for smoke alarm systems, when operating in a different negative current mode as indicated by meter 29. That is, this instrument operates differently from the prior art smoke detectors in that positive direction ion current flow (of the opposite polarity) and dynamic current flow changes must be detected. Thus completely different detection means is required, and furthermore these units have not been used to provide a standard of alpha emission for comparison quantitatively with influences of external alpha radiation at high degrees of accuracy and at very low critical signal magnitudes.

In this embodiment the air flow path 30, which could contain radon daughters (Rn), for example, passes through gateway 31, and optional filter 32 through the outer anode electrode 17 into the alpha particle activity chamber 16. To determine quantitatively the concentration of alpha radiation or other ingredients such as molecules in the air flow path which affect ionization in the alpha particle activity chamber 16, the air flow is timed and measured accurately by suitable air flow speed and dimensions, over a time period such as one minute, and a reading taken is quantitatively related to the signal allocated per unit of air. Thus, a sensitive and accurate instrument is provided for measuring very minute concentrations of pollutants or other ingredients in air, such as radon, alpha radiation, ions and other phenomena affecting the magitude of current I (22) from the detector electrode 21 by reactions occurring in the alpha particle activity chamber 16. For example, accurate measurements of radon gas concentration in air at radiation levels of 4 picocuries per liter are detectable from current flow I (22) from contaminated air flow streams passing into the alpha particle activity chamber 16 for interaction with the level of activity provided from the alpha source standard 14.

Figure 2:
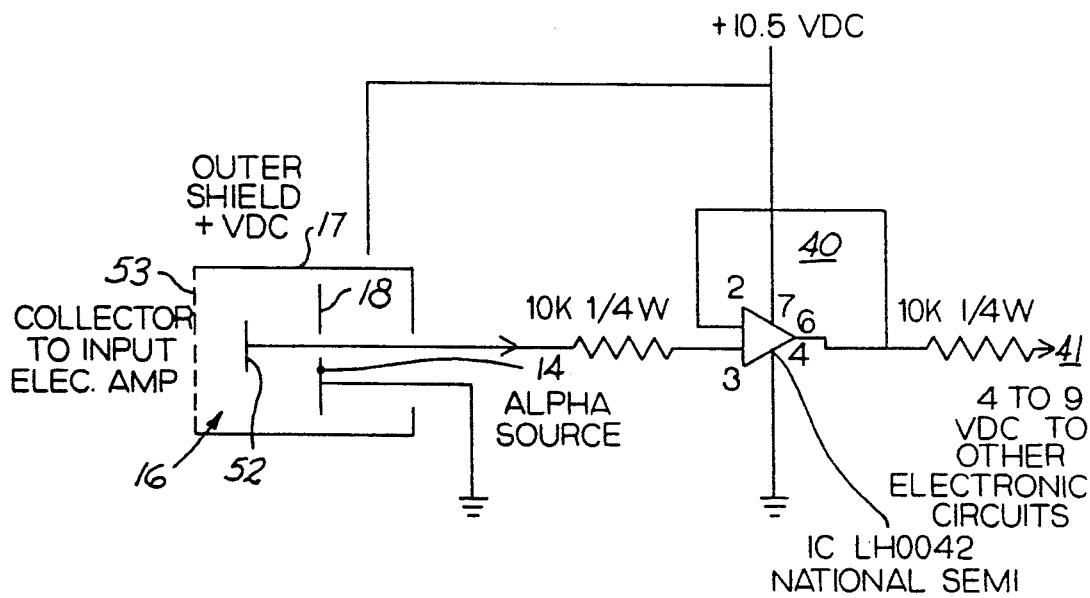
FIG. 2 is a schematic circuit diagram of an alpha detector and accompanying output signal amplifier afforded by an embodiment of the invention.

The instrumentation and method of detection is more amply set forth by reference to the partial system diagram of FIG. 2, wherein operational amplifier 40 isolates and relays the detected activity in chamber 16 to an output system 41. The configuration of the detector cell is schematically shown to represent a tubular outer anode 17, preferably of stainless steel, in which the perforated collector passageway 53 at one end of the tubing permits air and radiation to pass into the alpha particle activity chamber 16 biased by the standard emission source 14. The perforated collector portion 53 of anode electrode 17 is at a positive potential such as +10.5 volts direct current. The detector electrode 52 is appropriately spaced within the activity chamber 16 to detect differences in prevailing ionization levels affected by the alpha source standard 14, so that changes of the current (positive 29, FIG. 1) processed by operational amplifier 40 represent detected signal levels used in accordance with this invention to both identify alpha radiation and particular ioized molecules in the air flow path entering collector 53 and to quantitatively measure the concentration magnitudes thereof.

The cathode electrode structure 18 is at ground potential, at the negative potential level of the direct current source (23, FIG. 1). The integrated circuit 1CLH0042, available from National Semiconductor, permits operational amplifier 40 to relay the current flow status from detector electrode 52 and convert it to an output potential in a range of 4 to 9 volts D. C. without loading on the detector that could significantly change the linearity or accuracy of output measurements of very small changes in current.

Figure 3:
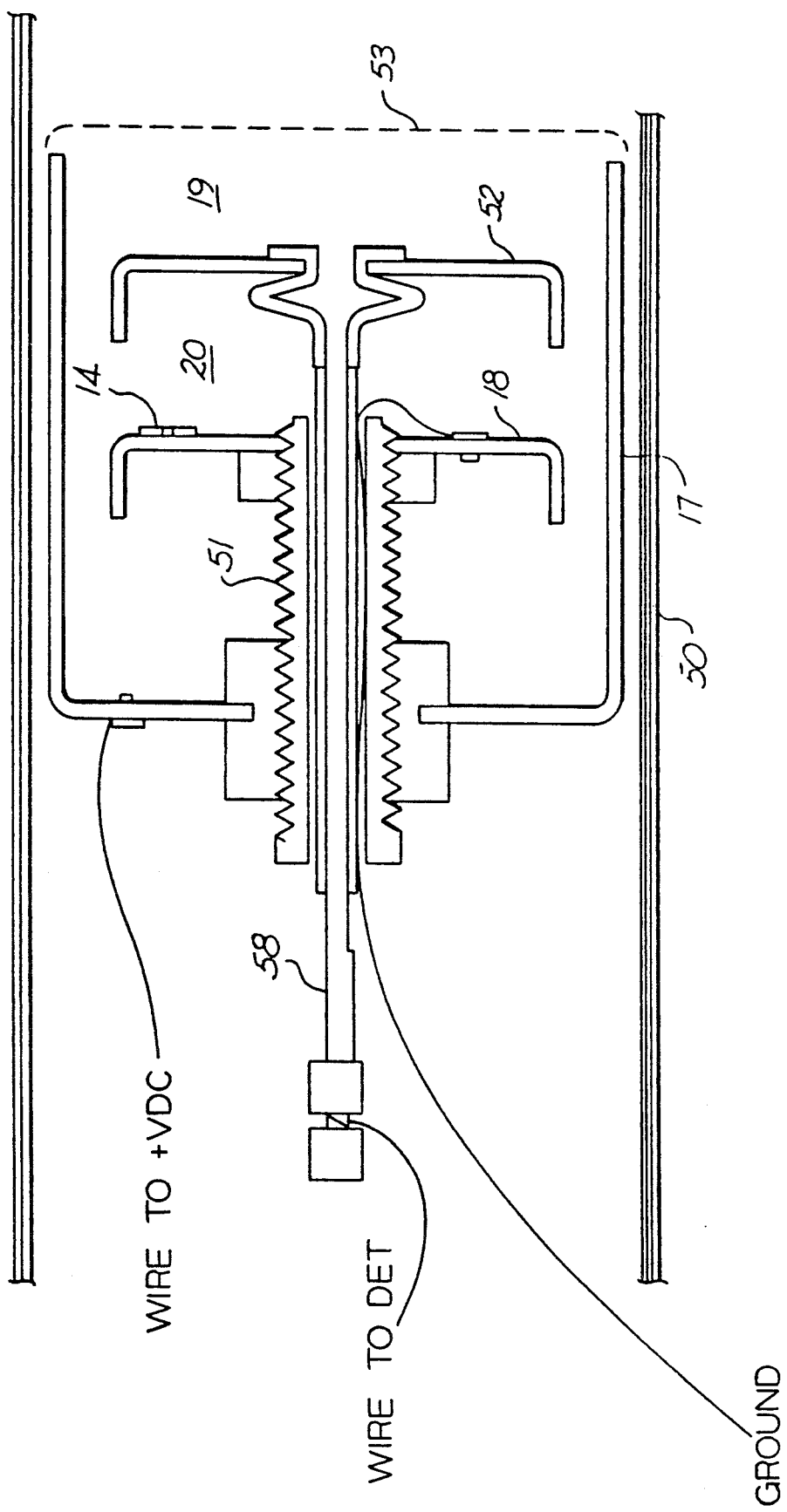
FIG. 3 is a cut away side view diametrical section sketch of an assembled cylindrical detector assembly configuration.

The physical embodiment of one cell configuration is shown in FIG. 3, where a view is taken through the axis of a stainless steel cylindrical outer housing electrode 17 being one inch (2.54 cm) in diameter. An outer grounded shield 50 has a metal foil 0.003 inch (0.008 cm) thick positioned between 0.003 inch (0.008 cm) layers of insulation of plastic such as "MYLAR" brand.

The inner grounded cathode electrode 18 of disc like configuration is fixed in place relative to the outer housing electrode and other electrodes by the mounting structure 51. Insulating portions such as the mounting screw are of a plastic such as sold onder the "NYLON" brand. The metal parts of the mounted electrodes are of stainless steel. The detector electrode 52 is movable axially by means of shaft 58, as a matter of adjusting the sensitivity range of the detector. The grounded cathode electrode 18 carries the alpha radiation standard 14, which is directed to emit radiation of alpha particles toward the sensing electrode 52 and anode screen 53 by means of a 1/16 inch (0.16 cm) diameter hole in a cover cap of a compartment containing the standard, such as a one microcurie standard radiation source model number AM241 available from the aforesaid supplier.

The open end shield screen 53 is of a wire mesh electrically connected with the outer anode electrode 17. Thus, the sensitive end of the detector is at the open screen end. The screen permits alpha radiation to penetrate the interior sensing compartment 19, which together with compartment 20 between electrodes 18 and 52 provide the region of alpha particle and associated ionization activity.

For a sensitivity enabling 4 picocurie per liter of air range a alpha radiation, the sensing electrode 52 is placed 0.2 inch (0.5 cm) from the outer screen 53, with the grounded cathode electrode 18 placed one half inch (1.27 cm) from the screen 53. The overall length of the outer anode electrode body thus in one inch (2.54 cm).

Two such cells may be mounted in a common container as hereinafter described with appropriate openings for permitting influx of air to pass by both cells, if desired as a function of a calibrated or metered pump for measuring air flow volume. This then provides a basis for comparison of one cell wherein unknown ingredients are being identified with one that is subjected to the same environmental conditions such as temperature and ambient air constituency and electrical voltages, etc. for assuring that output readings are accurately made without errors introduced from the environmental conditions.

This cell in operation has been found to reject radioactive radiation other than alpha radiation, such as gamma radiation and thus constitutes a selective alpha radiation meter that does not respond to other forms of radioactive radiation. Accordingly, no artificial forms of compensation, calibration or adjustment are required under conditions where other forms of radioactive radiation, for example gamma, are present.

Figure 4:
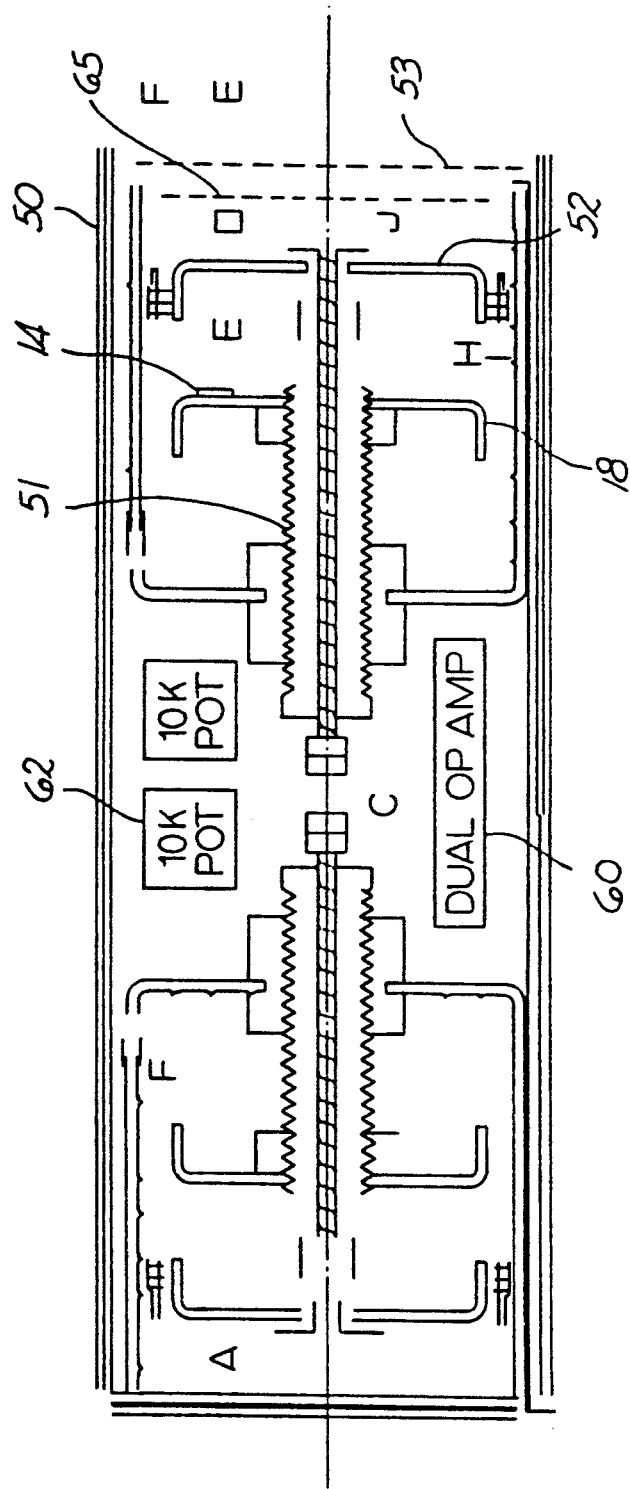
FIG. 4 is a is a side view sketch diametrical section sketch, partly in block schematic form of a dual cell stabilized detector assembly configuration having a range control electrode.

Such a duel cell arrangement is shown in FIG. 4, which can be made with internally arranged potted printed microcircuit structure such as operational amplifiers 60. Voltage adjustment balancing potentiometers 62 permit making initial factory adjustments to account for variances in manufacturing tolerances, etc. It is generally known how to connect such cells for stabilizing response, such as set forth in the parent patent above identified.

The two cells are identical in configuration and are matched for identical performance in the presence of pure air. The reference cell, on the left in FIG. 4, has a small hole to insure that both cells have identical air pressures.

Of significant interest in this cell configuration is the additional range control electrode 65 which permits this very sensitive detector to respond for accurate direct quantitative measurements of a wide range of signal strengths such as alpha radiation, and the like.

Figure 5:
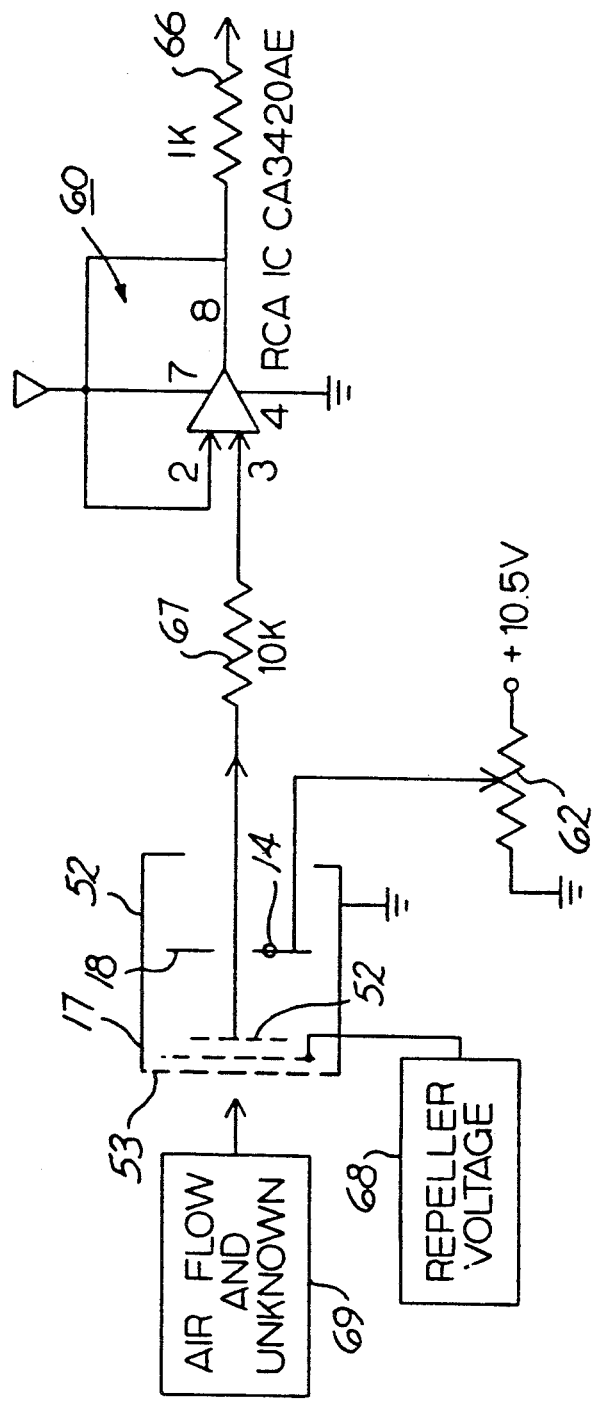
FIG. 5 is a schematic circuit diagram, partly in block, of an operational control circuit for such detector cells having range control electrodes.

In the operational amplifier configuration of FIG. 5, the RCA model CA3420AE integrated circuit operational amplifier 60 illustrated provides an output voltage swing of one to eight volts by way of isolating resistor 66, which varies linearly as a function of the input proton energy detected at resistor 67 in response to the alpha particle bombardment of the collector electrode 52.

With an AM 241 (<1 micro-curie 5.5 MEV with a half life of 433 years) as the standard radio-isotope source and a variable potential direct current source at potentiometer 62, a one time adjustment at the factory is made to compensate for the differences in source, variations in cell dimensions, and for amplifier operating variations inherent in manufacturing, etc. The potentiometers are potted with PCB and sealed in the cell housing. Air is the carrier. The detector electrode 52 is typically a lipped collector 0.9 inch (0.2 cm) in diameter with a lip of 0.2 inch (0.5 cm) and a thickness of 0.025 inch (0.006 cm). The detector sensitivity is determined by the ratio of parallel bias surface of the collector lip to the cell wall that is at ground potential, collector pickup area, distance of the pickup area surface to the cell wall, the distance and potential of the D. C. source used in the bias network, and to a lesser extent the input current of the detection amplifier 60.

Operation of the range control or repeller screen 65, preferably stainless steel along with the entranceway mesh 53 to reduce the propensity to release proton energy from alpha radiation, is achieved by means of repeller control means 68. This electrode is normally held at ground potential along with the outer shield 17 and entrance mesh 53 for admitting the unknown source of radiation, or the like 69 in the standard highest sensitivity range. A calibrated negative potential in six decades of dynamic range is applied to the repeller screen 65 by means of a potential transistor circuit arrangement. Typically with the grounded repeller range control electrode 65 a range of 100 counts per minute (CPM) to 500,000 CPM is available without saturation. Thus the six decades can provide for strong signals of up to 5,000,00 CPM, with each range providing linear output voltage readings from two to nine volts.

Figure 6:
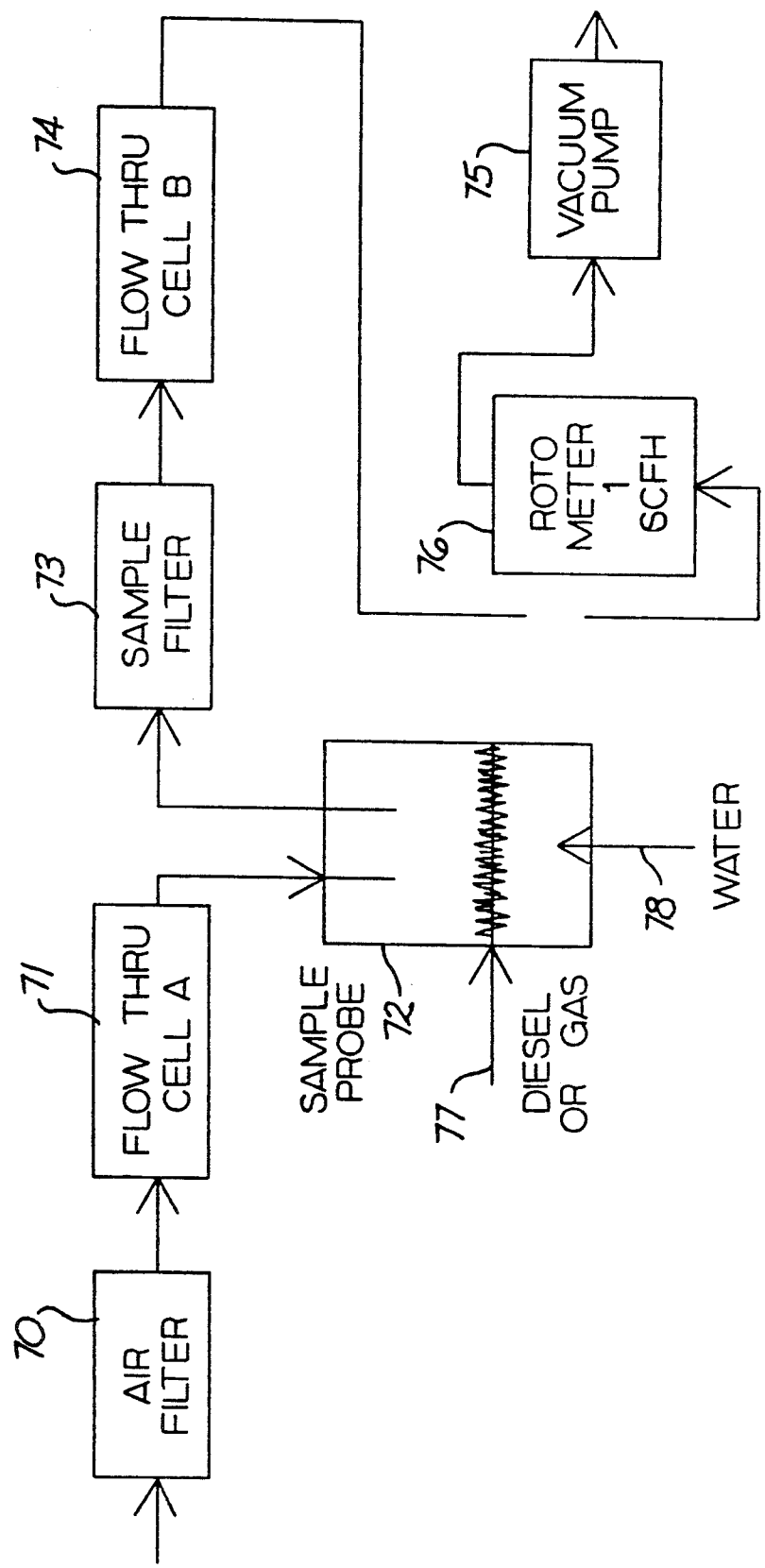
FIG. 6 is a block circuit diagram of a gas fingerprinting detection system afforded by the invention using a dual cell embodiment such as shown in FIG. 4.

As may be seen in FIG. 6, the cell pairs 71, 74 can be used for quantitative measurement of unknown gases by measurement of the air flow through the cells to produce output signals directly in terms of radiation per unit volume, for example, picocuries per liter of air. The air filter 70 removes dust, moisture, etc. and provides pure air flow without unwanted unknown non-gaseous ingredients including oil that could interfere with detection or quantification of unknown gases 77 which are to be processed. Air flow through the reference cell 71 provides an adjustment for pressures of air, temperature, and other ambient conditions that could otherwise cause errors in output signals and is so connected in a conventional manner.

In the sample chamber 72, into which the unknown gas 77 is introduced, preferably by passing through a water bath 78 and otherwise filtered at 73 to remove oils or other contaminants that could affect the cells or accuracy of measurement. Thus the unknown gas is identified and quantitatively measured in cell 74 in conjunction with the vacuum pump 75 and air flow meter 76.

Figure 7:
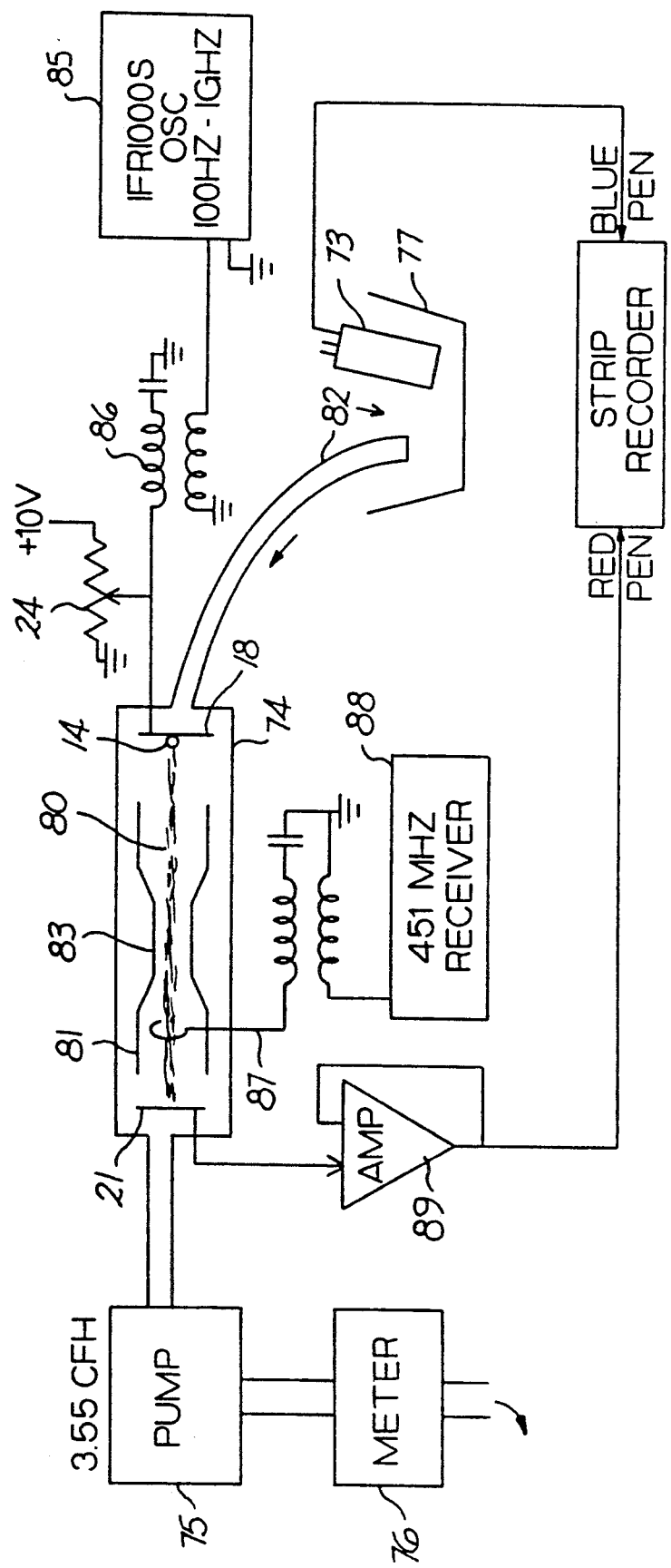
FIG. 7 is a block system diagram of a gas fingerprinting system afforded by the invention.

In FIG. 7 the general gas molecule fingerprinting system of this invention is shown. As related to FIG. 6, the two detector cells 73 and 74 and gas chamber 77 are shown with a flow through path calibrated by means of pump 75 and meter 76. The detector cell 74 is shown in more detail.

It is known from the U.S. Pat. Nos. 4,385,516; 3,634,754; and 4,007,624, supra, that radiation of a frequency related to individual unique molecule characteristics or resonance can be absorbed by the molecules to thereby identify them, or alternately may excite the molecules to become ionized so that they recapture free electrons to change current flowing in an alpha radiation induced ion stream. Thus, the molecules may be identified or fingerprinted by means of a known frequency, either by identifying ion currents, electron capture currents or by determining absorption of electromagnetic radiation at a resonance frequency which identifies the particular molecule or detecting its molecular radiation in the excited state. It is in this manner that the molecules are identified in this invention. However this prior art cannot effectively identify and quantize the presence of particular gas molecules in low concentration in free air.

For example, the radiation system of patent 4,385,516 does operate in atmospheric air, but it is subjected to electrostatic and electromagnetic interferences and such low emitted signal levels from ionized molecules that they may be lost in surrounding noise. The quantitative measurements by this method cannot be dependable or sensitive enough to determine very low concentration levels of the molecules of an unknown gas.

The requirement for laser energy in patent 4,007,624 and a massspectrometer makes the system prohibitive in cost and impractical to use outside a laboratory environment in such applications as in-situ monitors in the vicinity of gas storage tanks, pipelines or refrigeration systems that may leak and pollute the environment.

The conventional electron capture detector in patent 3,634,754 is limited in operation to ionization of a gas from collisions with alpha particle radiation in the ionization cell, and measurement of ion current flow between anode and cathode electrodes, and thus has very poor sensitivity to low gas concentrations and incapability of recognizing or fingerprinting particular gas molecules.

Therefore the present invention produces a new principle of detection of gas within the ionization cell which gives unexpected simplicity and sensitivity. That principle of detection within the cell 74 is now addressed. The alpha radiation path 80 between the cathode-alpha source electrode 18 and the detector or collector electrode 21 is identified within an air flow passageway 81 for processing gases in air at beaker 77 passing through flow pipe 82 into the cell 74. Thus the alpha stream 80 and the air flow path at restriction 83 is commonly caused to interact with greater efficiency than in an unrestricted space common in prior art ionization cells.

In accordance with this invention the ionization of gaseous molecules is enhanced while in the alpha stream 80 by modulating the identifying gaseous electron rings at a particular frequency with electromagnetic radiation from the radio frequency signal generator 85 suitably coupled into the cathode electrode by which the gas flow stream passes to enter the alpha stream. It is to be recognized that the cells are critical in dimension and very small in diameter to properly process the very high frequency electromagnetic energy involved in the required molecule fingerpriinting range of megaherz to giga herz. Also the coupling and transmission of the energy as signified at 86 by suitable radiofrequency links is critical for broad band pass over the frequency ranges that identify the resonance frequencies of various gas molecules and permit identification of broad band alpha particle contamination. The distributed capacities and inductances of the electrodes and wiring paths must be engineered to handle the frequencies involved. The cell thus is very much smaller than the heretofore described examples for use with such high frequency radiation.

Figure 8:
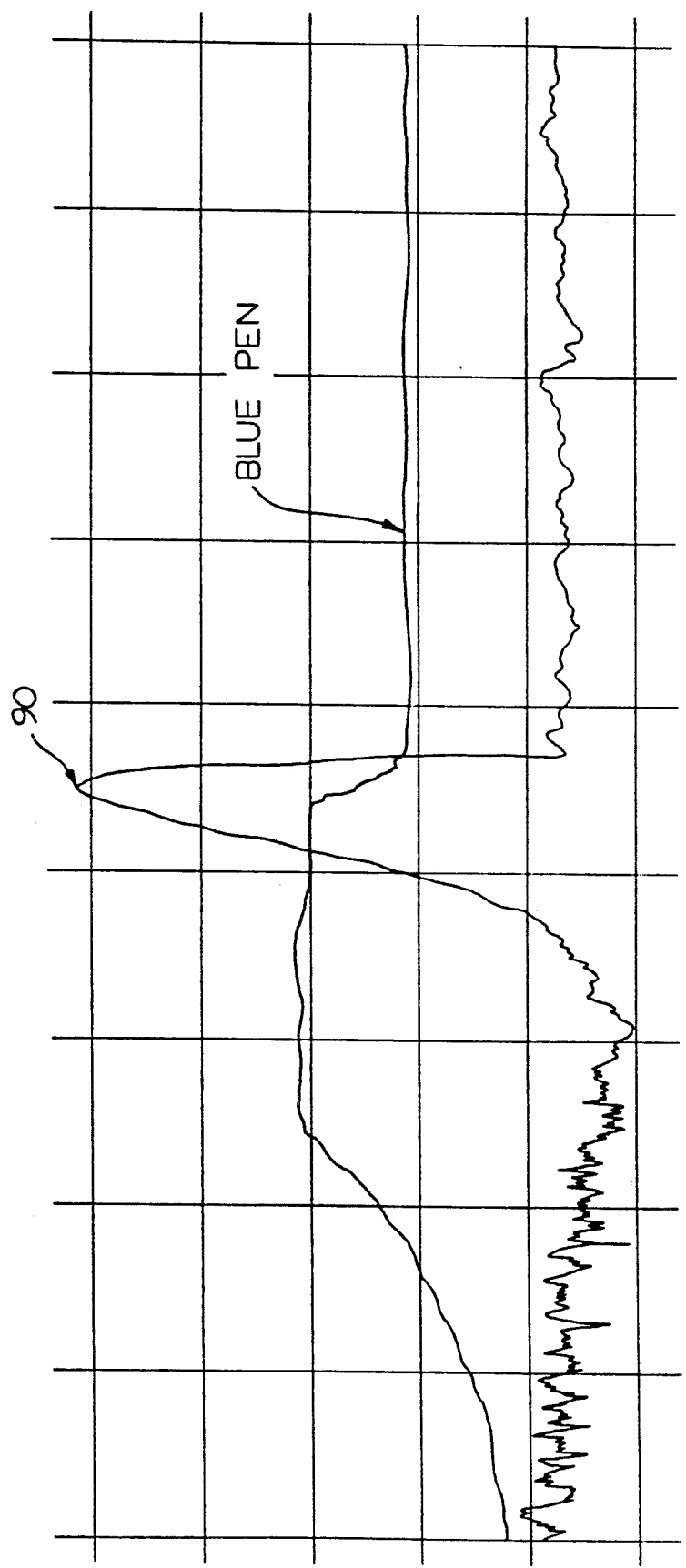
FIG. 8 is a waveform diagram of a fingerprint of a particular gas produced in accordance with this invention.

An r-f pickup probe 87 within the alpha activity region where the gas-air mixture and alpha radiation ion flow paths are interacting is used to monitor dynamic current variations by way of r-f receiver and f-m demodulator 88. The output signal from collector 21 is amplified at 89 for reproduction by the red pin on a two pen comparative strip recorder. The comparison cell 73 supplies a reference signal on the blue pen of the recorder. The strip chart output signal 90 of FIG. 8 results in the presence of a resonance frequency identifying a particular gas, in this case $CCl_2F_2$. The amplitude of the response determines the concentration magnitude of gas present and the frequency at which the response occurs identifies the resonance frequency or fingerprint of the particular gas molecule.

Figure 9:
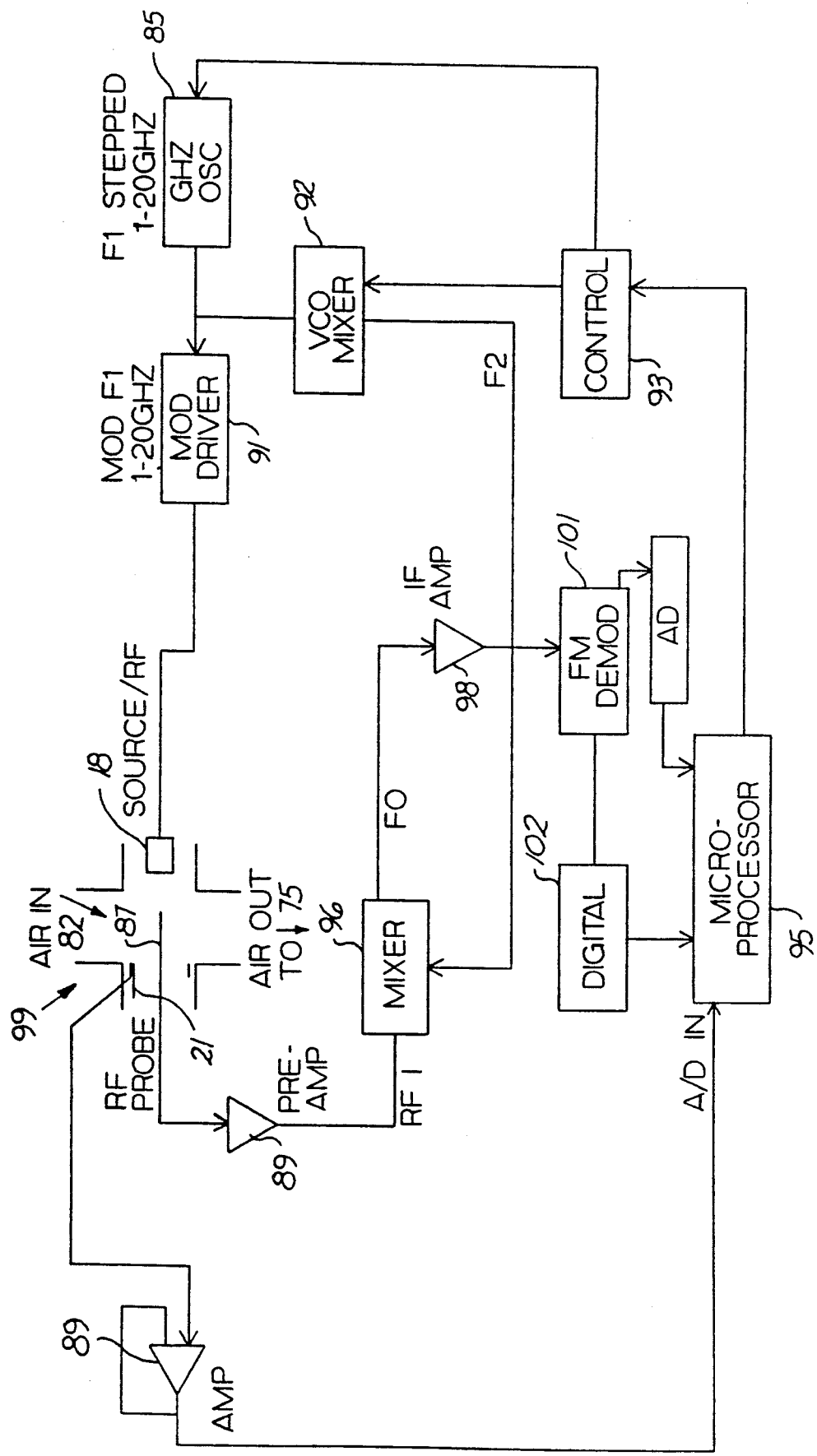
FIG. 9 is a block diagram of a harmonic detector system used in this invention to fingerprint particular gas molecules.

A block diagram of the r-f control system is shown in FIG. 9. The detector cell is shown schematically at 99, with the cathode-alpha source electrode 18 and the detector-collector electrode 21 positioned to react in an air flow path with input 82 and output 75. The air flow may be stationary or moving up to a velocity in excess of 500 cc per minute. The cathode 18 serves as an r-f antenna or input radiator and the r-f probe 21 as a monitoring output for detecting the reaction between the r-f signal and the alpha particle activity region through which the air flows. Thus, absorption or emission of r-f electromagnetic energy by particular gaseous molecules can be monitored for fingerprinting their identity.

In operation the variable frequency oscillator 85 is stepped through a range of selections in the frequency range of one to 20 gigaherz to provide a known frequency for matching fingerprints of various gas molecules in the manner described. Typically 255 steps are available. The modulator driver 91 then supplies the electrode 18 with a calibrated frequency r-f signal F1.

This frequency is scanned under control of tuning-control circuit 93 from the microprocessor 95, so that automatic scanning cycles may be introduced in a search mode to determine the identity of an unknown gas molecule, or the constituency of the gases in the air stream through the detector cell. Thus, typically the mixer frequency is scanned at a one Khz rate to develop a beat frequency scan signal F2 of 10.7 Mhz to 500 Mhz. The detected RF1 signal is thus mixed at mixer 96 to produce the resultant i-f frequency of 10.7 Mhz.

For processing in the computer-microprocessor 95, the signals are digitized internally, such as the A/D input from amplifier 89, which relays the monitorized effect of the electron current flow at collector electrode 21 in the presence of r-f activity in the alpha stream activity region of the detector cell 90. In this manner the dynamic changes when resonance frequency of a particular molecule occurs (90, FIG. 8) the microprocessor will store the frequency identification and the magnitude of the response and convert it into an identified gas molecule of quantified magnitude by matching with a stored spectral table.

Examples of resonance fingerprints are as follows:

Chlorotrifluoromethane $CClF_3$ resonance values 3,335.56 Mhz; 20,010.84 Mhz and 26,669.78 Mhz.

Trichlorofluoromethane $CCl_3F$ resonance values 2,465.39 Mhz; 9,853.68 Mhz and 14,790.46 Mhz.

Harmonics of the resonance values may be identified as picked up by r-f probe 87 through broad band preamplifier 89 to be heterodyned with mixer 96 signals to produce the 10.7 Mhz intermediate frequency for amplification at 98.

F-m demodulator 101 reproduces the scanned spectra and digitalizes the signals at 102 for input to the microprocessor 95. The microprocessor also may control and monitor the flow of air as shown in FIG. 7, so that the magnitude of the signals is directly related to the concentration of the unknown per unit volume of air.

This invention therefore has provided alpha stream type detector cells and corresponding detection systems for identifying and quantifying radiation, including alpha radiation and radiation absorption or emission induced by r-f excitation in gaseous molecules, which permits identification and quantification at very small concentrations of constituents in air. Those features of novelty which set forth the nature and spirit of the invention are defined with particularity in the following claims.

I claim:

1. A radiation detection system for detecting and quantizing the presence of unknown molecular particles in air at atmospheric pressures, comprising in combination: a cell housing having an entry way for introducing a stream of air into the housing at substantially atmospheric pressure; radiation means for introducing external radiation into the housing; a set of electrodes comprising an anode, a cathode and a detector electrode for monitoring free electrons within the housing; a calibrated alpha radiation emission standard source producing an ionization within the housing that induces free electrons at the detector electrode; means for interacting the stream of air and external radiation and the alpha radiation induced ionization in an alpha radiation activity region within the housing to dynamically affect molecular particle activity in the stream of air to produce emission of free electrons and detection of the free electrons at the detector electrode, and means for identifying the presence of specific particles introduced within the housing through said entryway by analysis of dynamic signals detected at said detector electrode in response to the external radiation introduced into the housing.

2. The detection system of claim 1 wherein said unknown molecular particles comprise a concentration of unknown gas molecules carried in the air stream, said means for introducing external radiation) further comprises means for producing radio frequency radiation in the housing of a variable frequency range for inducing an identifying resonant reaction in particular gaseous molecules, and said means for identifying the presence of particles further comprises means for comparing the magnitude of the dynamic response at the detector electrode with an identifying resonant frequency to determine the presence of specific gaseous molecule particles present in the air stream.

3. The detection system of claim 2 further comprising calibrated air pumping means for determining the air flow through the cell housing, and means for converting the detector electrode dynamic signals into a measurement of concentration per unit air of measured particles.

4. The detection system of claim 2 further comprising a strip recorder responding to a magnitude of electrons detected at said detector electrode in the presence of r-f radiation of a known frequency for quantitatively measuring the magnitude of concentration of said specific gaseous molecule particles in the air stream.

5. The detection system of claim 1 wherein said radiation means for introducing external radiation further comprises an r-f antenna within said housing and means for radiating from the antenna a frequency in the range of one to twenty gigaHz.

6. The detection system of claim 5 further comprising an r-f pickup probe within the housing in said alpha radiation activity region for detection of r-f activity.

7. The detection system of claim 5 further comprising a variable frequency oscillator coupled to the antenna for producing a frequency within said range, means for scanning the frequency through a frequency range including that known to identify particular gas molecules by their resonance response, and means coupled to said pickup probe for determining r-f response in the region of the alpha particle activity during a period of scanning the frequency range.

8. The detection system of claim 7 further comprising means for converting detected responses at said detector electrode and said r-f probe into digital signals.

9. The detection system of claim 8 further comprising a digital computer for analyzing the digital signals.

10. The detection system of claim 9 further comprising frequency scanning control means for scanning said oscillator through said frequency range, and digital computer control means for correlating detected responses within said housing with the frequency of the oscillator.

11. The detection system of claim 1 further comprising, means locating said entry way to pass through the anode electrode, a range control electrode located between said detector electrode and the entry way in said housing, and range control means for varying the potential on the range control electrode to reduce the detection sensitivity of the detector electrode.

12. The method of identifying unknown particles and their concentration in an air stream at substantially atmospheric pressure comprising the steps of:

creating a alpha radiation activity region in the air stream of calibrated constant magnitude, introducing the unknown particles into said alpha radiation activity region, providing anode and cathode electrode means for monitoring the alpha radiation activity, interspersing an electron detecting electrode in the radiation activity region to determine the presence of free electrons, dynamically measuring free electron activity changes in the alpha radiation activity region at the detecting electrode in the presence of the unknown particles to determine the magnitude of the unknown particles, introducing r-f radiation into the alpha radiation activity region, and monitoring r-f radiation dynamic changes in the presence of particular gas molecules in the air stream entering the alpha radiation activity region.

13. The method of determining the identity of particular gaseous molecules in air at substantially atmospheric pressure comprising the steps of ionizing the molecules by excitation with r-f radiation to which those molecules resonate while in a region of alpha radiation activity of constant magnitude, and determining the dynamic effect of electron activity in the region to establish a magnitude of concentration of the molecules.

14. A particle detector cell comprising in combination, a source of ionizing radiation of constant magnitude, an anode and cathode for moving ions through a radiation activity region, a detector electrode located in said region to capture and measure free electrons as a dynamic indication of the presence of particular particles in the activity region that affect the ionization magnitude, and r-f radiation disbursing means in said activity region for existing particular gas particles into ionization with a radiation frequency related to orbital resonance in the gas particles.

15. A particle detector cell comprising in combination, a source of ionizing radiation of constant magnitude, an anode and cathode for moving ions through a radiation activity region, a detector electrode located in said region to capture and measure free electrons as a dynamic indication of the presence of particular particles in the activity region that affect the ionization magnitude, an air stream access path into said cell, and an electrode dispersed to inhibit the passing of charged particles into said air stream path thereby to decrease the sensitivity of detection of the cell to said free elections.

* * * * *